US008965402B2

(12) United States Patent
Vathsangam et al.

(10) Patent No.: US 8,965,402 B2
(45) Date of Patent: Feb. 24, 2015

(54) PHYSICAL ACTIVITY MONITORING AND INTERVENTION USING SMARTPHONE AND MOBILE APP (71) Applicant: University of Southern California, Los Angeles, CA (US)

(72) Inventors: Harshvardhan Vathsangam, Los Angeles, CA (US); Gaurav S. Sukhatme, Pasadena, CA (US)

(*) Notice: Subject to any disclaimer, the term of this patent is extended or adjusted under 35 U.S.C. 154(b) by 79 days.

(21) Appl. No.: 13/744,169

(22) Filed: Jan. 17, 2013

(65) Prior Publication Data

US 2013/0190008 A1 Jul. 25, 2013

Related U.S. Application Data (60) Provisional application No. 61/588,599, filed on Jan. 19, 2012.

(51) Int. Cl.
H04W 24/00 (2009.01)
H04W 4/02 (2009.01)
H04M 1/00 (2006.01)

(52) U.S. Cl.
CPC . *H04W 4/02* (2013.01); *H04M 1/00* (2013.01)
USPC ..................................................... 455/456.1

(58) Field of Classification Search
USPC ..................................................... 455/456.1
See application file for complete search history.

(56) References Cited

U.S. PATENT DOCUMENTS

| 4,578,769 A | 3/1986 | Frederick |
| 4,855,942 A | 8/1989 | Bianco |
| 5,033,013 A | 7/1991 | Kato et al. |
| 5,453,758 A | 9/1995 | Sato |
| 5,485,402 A | 1/1996 | Smith et al. |
| 5,527,239 A | 6/1996 | Abbondanza |
| 5,591,104 A | 1/1997 | Andrus et al. |
| 2006/0161079 A1 | 7/2006 | Choi et al. |
| 2007/0051369 A1 | 3/2007 | Choi et al. |

(Continued)

FOREIGN PATENT DOCUMENTS

KR 10-2009-0123711 A 12/2009

OTHER PUBLICATIONS

International Search Report and Written Opinion of the International Searching Authority (ISA/KIPO), dated Jun. 25, 2013, for PCT Application No. PCT/US2013/021425, entitled "Physical Activity Monitoring and Intervention Using Smartphone and Mobile App," filed Jan. 14, 2013.

*Primary Examiner* — Joel Ajayi
(74) *Attorney, Agent, or Firm* — McDermott Will & Emery LLP (57) ABSTRACT

A mobile software application may issue an alert when a user is not achieving a heath objective based on track movement of a mobile computer system that is running the application and being carried by the user and physical characteristics of the user. The software application may map information about the physical characteristics of the user to a user model and determine the energy being expended by the user based on the user model and movement information provided by the mobile computer system. The software application may determine the frequency of steps taken by the user by: bandpass filtering a time domain signal that is representative of the movement, transforming the filtered time domain signal into a frequency domain signal, and equating the step frequency with the frequency of the highest peak in the frequency domain signal.

7 Claims, 4 Drawing Sheets

(56) References Cited

U.S. PATENT DOCUMENTS

| | | |
|---|---|---|
| 2007/0179359 A1* | 8/2007 | Goodwin .................... 600/300 |
| 2009/0047645 A1 | 2/2009 | Dibenedetto et al. |
| 2010/0286488 A1* | 11/2010 | Cohen et al. ................ 600/300 |
| 2011/0046519 A1 | 2/2011 | Raheman |
| 2011/0288379 A1 | 11/2011 | Wu |

* cited by examiner

FIG. 3A  Forward Acceleration

FIG. 3B  Up-Down Acceleration

FIG. 3C  Sideways Acceleration

PHYSICAL ACTIVITY MONITORING AND INTERVENTION USING SMARTPHONE AND MOBILE APP

CROSS-REFERENCE TO RELATED APPLICATION

This application is based upon and claims priority to U.S. provisional patent application 61/588,599, entitled "DATA-DRIVEN ALGORITHM FOR CALORIE TRACKING USING INERTIAL SENSORS," filed Jan. 19, 2012. The entire content of this application is incorporated herein by reference.

STATEMENT REGARDING FEDERALLY SPONSORED RESEARCH

This invention was made with government support under Grant No. CCR-0120778, awarded by the National Science Foundation (NSF) and under Grant No. P60 MD 002254 awarded the National Center for Minority Health and Health Disparities (NCMHD). The Government has certain rights in the invention.

BACKGROUND

1. Technical Field

This disclosure relates to technologies that monitor physical activity and intervene to promote better health.

2. Description of Related Art

Many people want and/or need assistance maintaining and/or improving their health through physical activity. Unfortunately, obtaining that assistance has often been expensive, difficult, and/or inconvenient.

SUMMARY

A mobile computer system may include a movement detection system that does not rely on GPS signals. A downloadable software application may include a program of instructions that is configured to cause the mobile computer system when running the software application to receive information about physical characteristics of a user that carries the mobile computer system; track movement of the mobile computer system while being carried by the user based on movement information provided by the movement detection system; determine whether the user is achieving a heath objective based on the tracked movement and the physical characteristics of the user; and issue an alert to the user if the user is determined not to be achieving the heath objective.

The movement detection system may include an accelerometer and/or a gyroscope. The program of instructions may be configured to cause the mobile computer system when running the program of instructions to track movement of the mobile computer system based on movement information from the accelerometer and/or gyroscope.

The program of instructions may be configured to cause the mobile computer system when running the program of instructions to issue an alert to a person other than the user if the user is determined not to be achieving the heath objective by communicating the alert over a computer network system to the other person.

The program of instructions may be configured to cause the mobile computer system when running the program of instructions to receive an alert from a computer network system that a person other than the user has been determined not to be achieving a health object.

The program of instructions may be configured to cause the mobile computer system when running the program of instructions to provide information to the user indicative of the degree to which the user is achieving the health objective based on the tracked movement and the physical characteristics of the user.

The program of instructions may be configured to cause the mobile computer system when running the program of instructions to provide information to a person other than the user indicative of the degree to which the user is achieving the health objective based on the tracked movement and the physical characteristics of the user by communicating the information over a computer network system to the other person.

The program of instructions may be configured to cause the mobile computer system when running the program of instructions to receive information from a computer network indicative of the degree to which a person other than the user is achieving a health objective.

The program of instructions may be configured to cause the mobile computer system when running the program of instructions to receive information from a computer network indicative of the degree to which multiple persons other than the user are each achieving a health objective and to compute a group score indicative of the degree to which the multiple persons and the user are collectively achieving their respective health objectives.

The program of instructions may be configured to cause the mobile computer system when running the program of instructions to participate in a contest and to utilize the group score as a factor that affects the ability of the user to prevail in that contest.

The program of instructions may be configured to cause the mobile computer system to perform any of the functions described herein, except when delivering an alert, in the background while other programs of instructions are running in the mobile computer system.

The mobile computer system may generate a time domain signal that is indicative of steps that a user is taking while carrying the mobile computer system. The program of instructions may be configured to determine the frequency of those steps by: filtering the time domain signal so as to substantially attenuate frequencies that are lower than 0.5 Hz and higher than 10 Hz; transforming the filtered time domain signal into a frequency domain signal; equating the step frequency with the frequency of the highest peak in the frequency domain signal; and communicating the equated step frequency.

The program of instructions may be configured to cause the mobile computer system while running the program of instructions to transform the filtered time domain signal into a frequency domain signal using a fast Fourier transform.

The program of instructions may be configured to cause the mobile computer system while running the program of instructions to determine whether the user is walking or running by: filtering a low range of the time domain signal so as to substantially attenuate frequencies that are lower than 0.5 Hz and higher than 2.5 Hz; filtering a high range of the time domain signal so as to substantially attenuate frequencies that are lower than 2.5 Hz and higher than 10 Hz; transforming the low range filtered time domain signal into a low frequency domain signal using a fast Fourier transform (FFT); transforming the high range filtered time domain signal into a high frequency domain signal using a fast Fourier transform (FFT); determining that the user is walking if the low frequency domain signal has a peak signal that is larger than any peak signal in the high frequency domain signal; determining that the user is running if the high frequency domain signal has a peak signal that is larger than any peak signal in the low frequency domain signal; and communicating whether the user has been determined to be walking or running.

The time domain signal may be a composite of: a first time domain signal that is representative of movement of the mobile computer system in a first direction; a second time domain signal that is representative of movement of the mobile computer system in a second direction that is orthogonal to the first direction; and a third time domain signal that is representative of movement of the mobile computer system in a third direction that is orthogonal to the first and the second direction.

The time domain signal may be the signal that has the highest peak level among the following signals, as compared to the highest level peak of the other signals: a first time domain signal that is representative of movement of the mobile computer system in a first direction; a second time domain signal that is representative of movement of the mobile computer system in a second direction that is orthogonal to the first direction; and a third time domain signal that is representative of movement of the mobile computer system in a third direction that is orthogonal to the first and the second direction.

The program of instructions may be configured to cause the mobile computer system while running the program of instructions to communicate that the user is not taking steps if the highest peak in the frequency domain signal is not substantially higher than the other peaks in the frequency domain signal.

The time domain signal may be representative of only vertical movement of the mobile computer system. The program of instructions may be configured to cause the mobile computer system while running the program of instructions to determine the time domain signal based on information from the mobile computer system that is indicative of its orientation.

The program of instructions may be configured to cause a mobile computer system to determine energy being expended by a user while carrying the mobile computer system by: receiving information about physical characteristics of a user that carries the mobile computer system; mapping the information about the physical characteristics of the user to a user model; and determining the energy being expended by the user while carrying the mobile computer system based on the user model and movement information provided by the movement detection system that is indicative of movement of the user while carrying the mobile computer system.

The movement information provided by the movement detection system may include the frequency of the steps and the amplitude of the steps.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

DETAILED DESCRIPTION OF ILLUSTRATIVE EMBODIMENTS

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

Goals

A family of regression techniques may be used for the prediction of energy expenditure (e.g., number of calories burned) of a human body using inertial sensors. The inertial sensors may include accelerometers, gyroscopes, and magnetometers. These sensors may sense acceleration (accelerometer), rotational rates (gyroscopes) and magnetic fields (magnetometers). When worn on the human body, they may sense movement of the human body.

Such sensors may already be part of existing mobile communication systems, such as smartphone. A software mobile application may be downloaded and installed in these mobile communication systems that enable the energy expended to be determined, as well as to perform other tasks, such as notification tasks. Examples of specific algorithms and other functions that this software application may be configured to perform are described below.

Movement measured by these sensors may be characterized using movement descriptors. These descriptors may then be mapped to energy expended from human movement.

What may make the problem hard may be:

1. What are the right descriptors of movement?
2. How does one map movement to energy?
3. Even for the same movement, different people may burn a different number of calories. So how does one account for these differences among people?

One goal may therefore be to identify a functional mapping f:(Movement, Physiology→Energy). A set of algorithmic techniques is presented to quantify this map. For the rest of this document, a standard terminology is adopted that is used to describe different elements of the algorithms discussed herein. The terminology used in this document is summarized in the following table:

| Term | Description | Dimension |
| --- | --- | --- |
| p | Person p | 1 × 1 |
| $N_p$ | Total number of data points for person p | 1 × 1 |
| $n_p$ | $n_p^{th}$ datapoint for person p out of a total of $N_p$ datapoints | 1 × 1 |
| $x_{n_p}$ | $n_p^{th}$ movement descriptor for person p | D × 1 |
| $Phys_p$ | Physiological descriptors for person p | (M + 1) × 1 |
| $X_p$ | Collection of input data for person p | $N_p$ × D |
| $y_{n_p}$ | $n^{th}$ energy expenditure value for person p corresponding to movement $x_{n_p}$ | 1 × 1 |
| $Y_p$ | Collection of energy expenditure values for person p | $N_p$ × 1 |
| $\beta_p$ | Precision parameter for the mapping from $x_{n_p}$ to $y_{n_p}$ for person p | 1 × 1 |
| $w_p$ | Model parameter for person p | 1 × D |
| $\alpha_p$ | Precision parameter for confidence of model, $w_p$ | 1 × 1 |
| k | Population parameter matrix for generalization | D × M |
| X | Collection of all input data points | P × $N_p$ × D |
| Y | Collection of all energy expenditure values | P × $N_p$ × 1 |
| PHYS | Collection of all physiological values | P × (M + 1) |

A test population may consist of P participants. For each participant p, their corresponding physiological descriptor may be $Phys_p$ and training data points may be collected in the form of input-output pairs ($x_{n_p}$, $y_{n_p}$), where $n_p$ is the index of the $i^{th}$ datapoint for person p. Let there be $N_p$ data points collected for each person p. Thus for P participants, there may be a large dataset consisting of the energy values $Y_p = \{y_{1_p}, y_{2_p}, \ldots, y_{N_p}\}$ and D-dimensional descriptors of movement $X_p = [x_{1_p}^T x_{2_p}^T \ldots x_{N_p}^T]^T$. The following may be denoted: $Y = \{Y_1, Y_2, \ldots, Y_P\}$, $X = \{X_1, X_2, \ldots, X_P\}$, and PHYS = $\{[Phys_1^T Phys_2^T \ldots Phys_P^T]^T\}$ to be complete set of training data for all participants. Given this terminology, for a person p, at a given instant of time, given an example of their movement descriptor $x_{n_p}$ and personal physiology, $Phys_p$, a goal may be is to determine energy expenditure:

$(x_{n_p}, Phys_p) f \rightarrow y_{n_p}$.

A statistical approach to this mapping may be adopted, meaning that examples of various people performing different kinds of movement may be collected and their energy expenditure from a metabolic unit may be concurrently measured. A statistical model may be built that indicates what the distribution of energy expenditure is given their movement and physiology. The distribution of energy expenditure may be obtained viz. $p(y_{n_p}|x_{n_p}, Phys_p)$. The mean value, most likely value, the confidence of prediction, or any other relevant variable from this model can be calculated. The models may work with any kind of inertial sensor.

Here, a focus is on using movement detected and measured using the same sensors that are embedded in the cellphone. This may enable the number of calories burned to be determined using movement detected by the cellphone.

Reliable Frequency Spectrum-Based Reliable Extraction of Periodic Activities from Inertial Sensors This section tackles the issue of representation of movement, specifically, with the definition of what $x_{n_p}$ may be for a person p for periodic activities. Movement may be periodic and indicators of periodicity may be extracted. As a person moves and carries a phone on them, streaming inertial data may be received from sensor hardware at a sampling frequency F. This datastream may be $D(n), n \in \{1, 2, 3 \ldots\} \times \Delta T$, where $\Delta T = 1/F_s$ (in general, these data can be multi-dimensional).

—Data Pre-Processing

A primary concern may be detecting human movement. Raw data from any given inertial sensor may be filtered to exclude those frequency components of movement that do not belong to that particular activity. Depending on the activity that is being tracked, different kinds of filters may be used. For walking, a 2nd order Butterworth bandpass filter may be used with 3 dB cut-off frequencies between 0.75 Hz and 2 Hz. For running, cycling, and jogging, a 2nd order Butterworth bandpass filter may be used with 3 dB cut-off frequencies between 1 Hz and 10 Hz. Similar sets of frequencies can be chosen for any other periodic activity like ellipticals and rowing.

—Descriptors of Movement

—Fourier Transform-Based Descriptors

These data may be partitioned in real-time into data chunks or epochs $\epsilon_{n_p}$. Each epoch may consist of a subset of streaming inertial data samples that belong to a time interval $T_{n_p}$. Typical sampling rates may be between 15 Hz and 50 Hz depending on the time accuracy desired.

$D(\epsilon_{n_p}) = D(n), n \in (T_{n_p}]$.

The length of this time interval may be between 5 seconds and 1 minute depending on what kind of movement needs to be tracked. Time periods may be long enough to capture periodicities and short enough to capture variations in periodicities. Movements such as walking and cycling may require a minimum time period length of 5 seconds and a maximum time period of 20 seconds. Consecutive time intervals can also overlap. Typical overlap between intervals may be 10%-80%. 10% overlap may mean that 10% of the samples overlap between consecutive windows. For each epoch, the mean value of that epoch $D(\epsilon_{n_p}) \leftarrow D(\epsilon_{n_p}) - \mathbb{E}(D(\epsilon_{n_p}))$ may be subtracted to remove any DC components of the signal.

The absolute magnitude of the Fast Fourier Transform of the signal across each dimension may be calculated. For a given time series D(n), the N-point discrete Fourier transform may be given by $$\mathcal{F}(D(\epsilon_{n_p})) = \sum_{n=0}^{N-1} D(n) \cdot e^{-i2\pi \frac{k}{N} n},$$

where N is the length of the DFT. Lengths of the DFT may be 1024 points or 512 points. This may result in an N-point complex number. The magnitude of the fast Fourier transform may be obtained by taking the magnitude of each of the N points. $F(n) \leftarrow \|\mathcal{F}(D(n))\|, n \in [1 \ldots N]$. This may result in an N-point vector which each point corresponding to a particular frequency multiple. Components of the spectrum that are not necessary may then be removed. This may include low frequency components below 0.75 Hz and higher frequency components. Which higher frequency components are removed may depend on the activity in question, but may be the same as the frequency components used in the bandpass filtering. The FFT may be an efficient way to calculate the DFT using recursive rules.

The phone's orientation may be determined using a built-in rotation sensor in the smartphone, and the vertical component of movement may be extracted. Depending on the orientation, the time series from that dimension of the signal that correspond to movement in the vertical direction may be selected. For example, if recording the phone's three-dimensional accelerometer data and if the Y-axis of the phone's coordinate frame is vertical, then the fast Fourier transform corresponding to the Y-axis dimension of the accelerometer data may be picked. The highest peak in the fast Fourier transform signal may be picked and the corresponding frequency of this found. This may represent the period of the walk. If the orientation of the phone switches so that another axis is vertical, the peak finding operation may be switched to another series. A similar operation can be carried out using a three dimensional gyroscope data. The accelerometer data may be the preferred time series, but in the absence of accelerometer data, gyroscopic data can be used. The peak that is calculated may correspond to the average step frequency in that epoch.

A "smart" approach may be used where the phone is reoriented to a canonical vertical position using the phone's orientation information. This may involve applying an inverse rotation operation (based off the phone's current orientation) on the original data to rotate the axes to a canonical vertical position. The rotation may be applied before bandpass filtering of data. All the previously described operations may be performed on the vertical direction of this de-rotated, bandpass filtered signal.

The Fourier transforms may be combined in one of these ways:
1. Add Fourier transforms from multiple axes to reinforce periodic components.
2. Multiply Fourier transforms from multiple axes to remove spurious components (corresponds to convolution or measure of overlap between components).
3. Append Fourier transforms of multiple axes one after the other to retain all periodic components From these, the largest value of the combined Fourier transform can be extracted and the peak corresponding to that vector can be ascertained. This technique may require a minimum of 5-6 periods of the activity in question. The combined Fourier transforms from each epoch may represent the input data point $x_{n_p}$ for that epoch to be used in algorithms described later. With respect to inertial data, the two most important time series may be acceleration in the up-down direction and in the forward direction. For rotational rates, rotational twist corresponding to the vertical axis may be the best, but may not be as good as accelerations.

—Other Techniques
Other approaches include:
1. Obtain the autocorrelation signal of each data's dimension within each epoch and then calculate the lag value of the second largest peak after the 0 lag peak. This may provide the time period of oscillation.
2. Obtain the autocorrelation signal and the absolute magnitude of the Fourier transform from the previous section and determine frequency candidates from each. Use dynamic programming to determine which of those makes sense. This may be similar to the YAAPT pitch tracking algorithm.
3. Use peak detection of the absolute magnitude of the acceleration/gyroscopic signal, count how often a peak occurs within a time epoch, and record that as the periodicity. An extension to this may be to compare consecutive signal segments that are partitioned by peaks and determine if they are similar to each other. This may be in a time sense by using the dynamic time warping algorithm or in a space sense using the Euclidean distance between them.
4. Learn motifs from the segments (using some sample data) created by the peak detection algorithm and then slide the pattern across the datastream. As the motif is slid, the dynamic time warping distance may be continuously calculated between the motif and the current data on which it is overlaid. If this distance is less than some value, then a period may be detected. Counting these periods in a time interval may identify the periodicity.
5. These techniques can be combined with the original frequency based technique by averaging (or weighted-averaging) the step frequency values that is returned from each of them.

Figure 1:
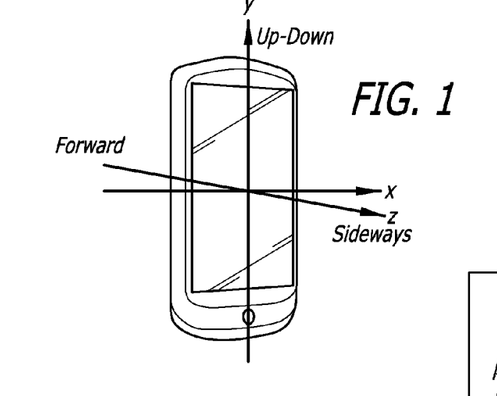
FIG. 1 illustrates an example of a smartphone oriented such that its Y axis is vertical.

FIG. 1 illustrates an example of a smartphone oriented such that its Y axis is vertical. The peaks of Y-axis movement may be tracked and the maximum peak in this tracking may be extracted to get the frequency component of this movement.

Figure 2A:
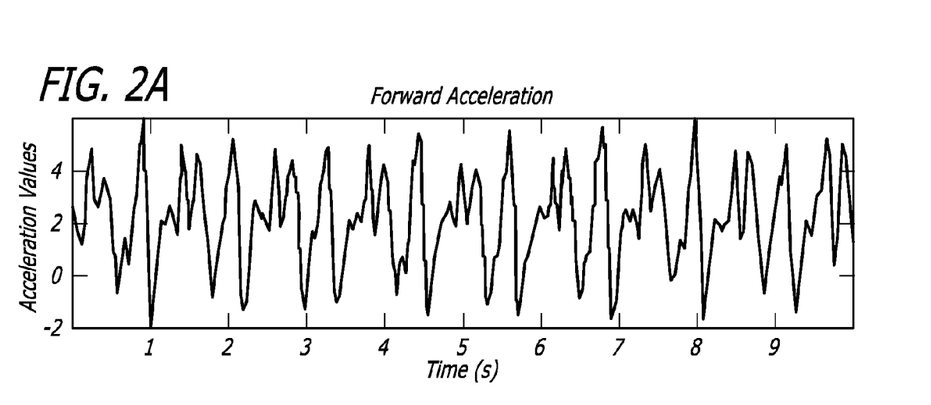
FIGS. 2A-2C illustrate an example of raw data coming from an accelerometer inside of the smartphone illustrated in FIG. 1 while being moved by a user.
Figure 2B:
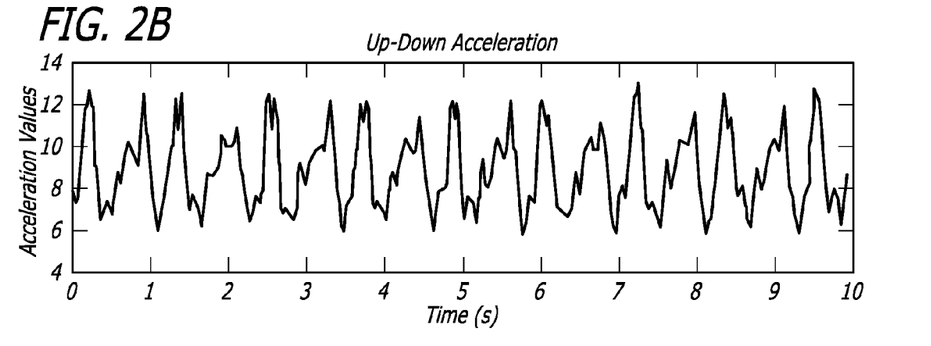
Figure 2C:
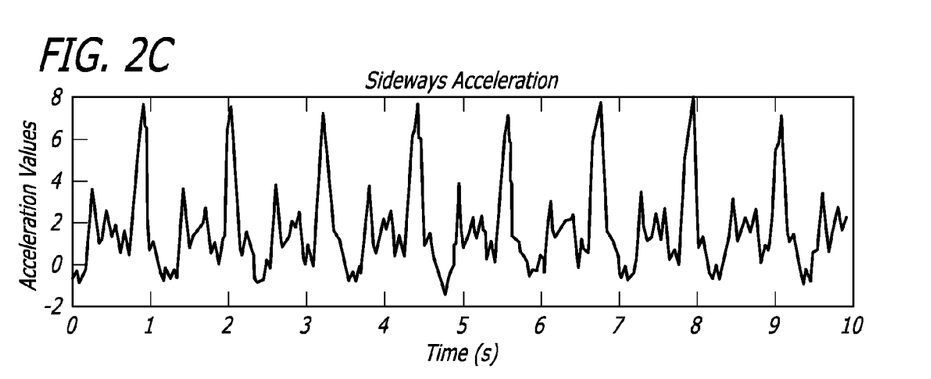

FIGS. 2A-2C illustrate an example of raw data coming from an accelerometer inside of the smartphone illustrated in FIG. 1 while being moved by a user. FIG. 2A illustrates the forward acceleration component; FIG. 2B illustrates the up-down acceleration component; and FIG. 2C illustrates the sideways acceleration component.

Figure 3A:
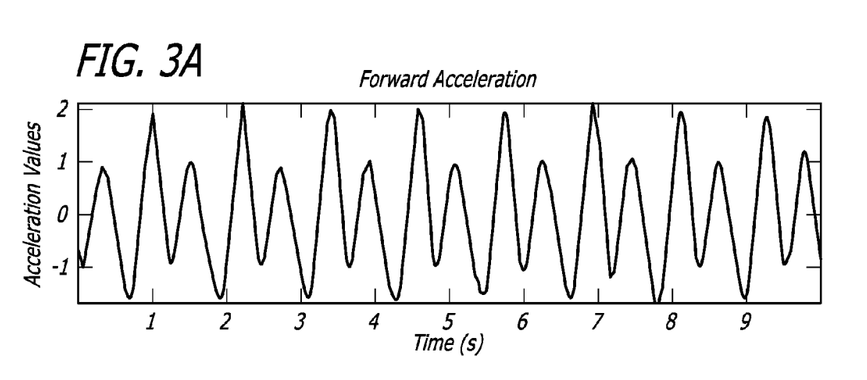
FIGS. 3A-3C illustrate the results of separately filtering each of the signal components that are illustrated in FIGS. 2A-2C, respectively, with a bandpass filter having cutoffs at 0.75 Hz and 2 Hz.
Figure 3B:
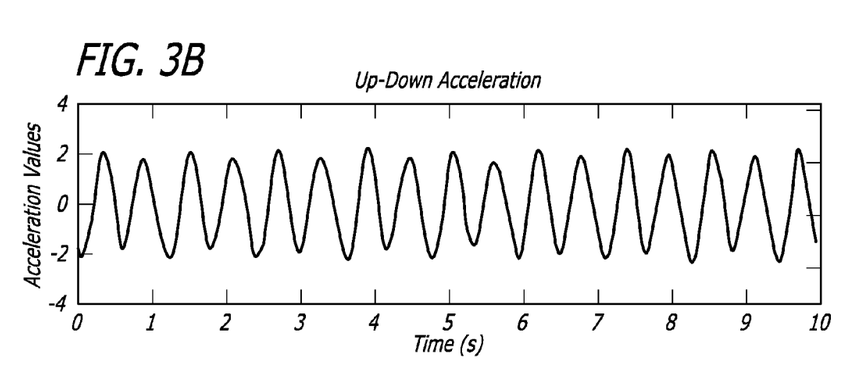
Figure 3C:
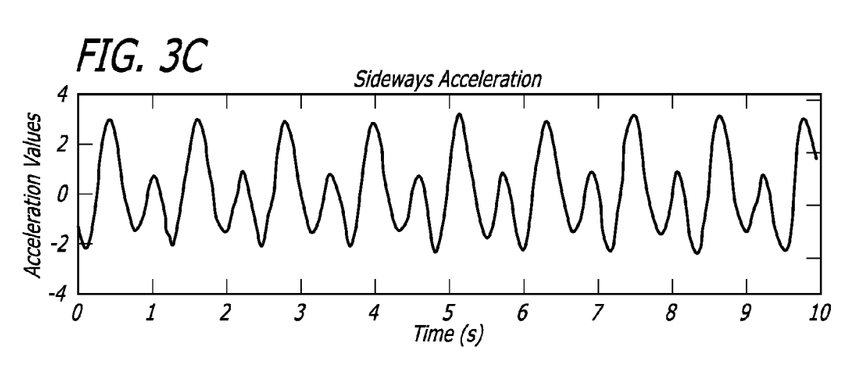

FIGS. 3A-3C illustrate the results of separately filtering each of the signal components that are illustrated in FIGS. 2A-2C, respectively, with a bandpass filter having cutoffs at 0.75 Hz and 2 Hz.

Figure 4A:
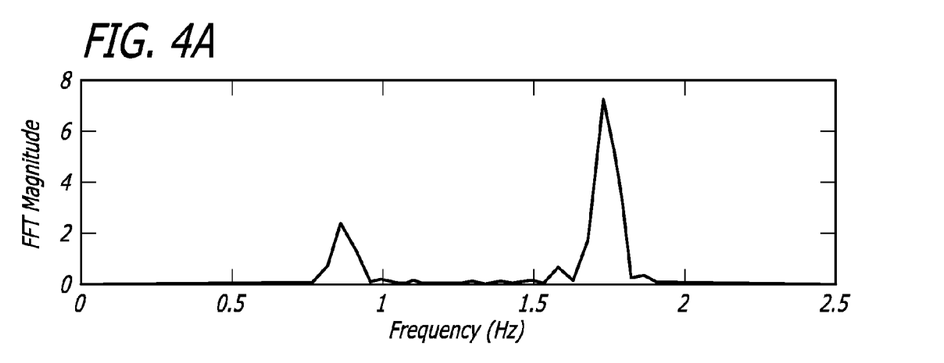
FIGS. 4A-4C illustrate the magnitude of a FFT extraction of the signals illustrated in FIGS. 3A-3C, respectively.
Figure 4B:
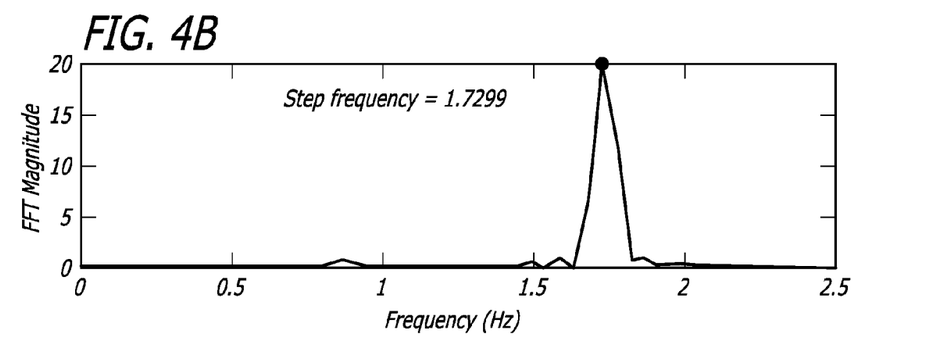
Figure 4C:
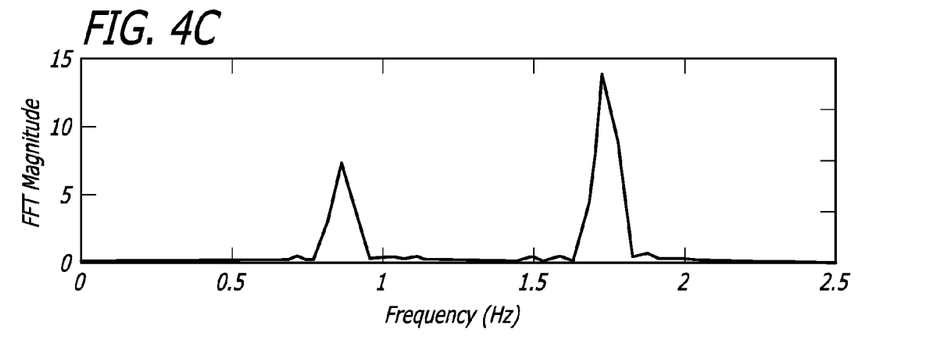

FIGS. 4A-4C illustrate the magnitude of a FFT extraction of the signals illustrated in FIGS. 3A-3C, respectively.

Personalized Energy Expenditure Models for Movement

In this section, one person at a time may be considered and a model for that person alone may be trained. Since the physiology of that person may be fixed, only the mapping from movement to energy viz. $p(y_{n_p}|x_{n_p})$ may be considered. Three such mappings may be considered—a linear model (Least-Squares Regression, LSR), a linear probabilistic model (Bayesian Linear Regression, BLR) and a non-linear probabilistic model (Gaussian Process Regression, GPR).

—Least-Squares Regression (LSR)

Linear model mapping a movement descriptor to energy expenditure may be expressed as:

$$Y_p = w_p^T X_p + \epsilon I, \epsilon \sim \mathcal{N}(0, \beta_p^{-1}) \qquad (1)$$

$$y_{n_p} = w_p^T x_{n_p} + \epsilon, \epsilon \sim \mathcal{N}(0, \beta_p^{-1}) \qquad (2)$$

where $\epsilon$ is a noise parameter, $x_{n_p} = (1, x_{n_p,1}, \ldots x_{n_p,D})^T$ is the derived function space consisting of fixed nonlinear functions of the input variables of dimension D, and $w_p = (w_{p,0}, \ldots, w_{p,D})^T$ are the weights. Given that $\epsilon$ is a Gaussian, allowing a probabilistic interpretation may mean:

$$p(y_{n_p}|x_{n_p}, w_p, \beta_p) = \mathcal{N}(y_{n_p}; w_p^T x_{n_p}, \beta_p^{-1}) \qquad (3)$$

An optimal fitting function may be defined as one that maximizes the likelihood that $p(Y_p|w^T X_p) = \Pi_{n_p=1}^N p(y_{n_p}|x_{n_p}, w_p, \beta_p)$. This may be equivalent to finding the optimal $w_p$ that would minimize the expected square-loss $E_D\{(y_{n_p} - f(x_{n_p}, w_p))^2\}$. The optimal prediction may be given by:

$$w_p = (X_p^T X_p)^{-1} X_p^T Y_p$$

The optimal prediction for a new data point $x_{*_p}$ may be given by:

$$y_{p*} = w_p^T x_{*_p} \qquad (4)$$

LSR may also be prone to the presence of outliers because it may not take into account the consistency of points in a dataset. Another drawback of LSR may be its tendency to over-fit to a given dataset due to which it often performs poorly on unseen data points. One solution may be to include a regularization term λ that controls the relative importance of data-dependent noise. However, finding the optimal λ may involve techniques such as K-fold cross-validation and the need to maintain a separate validation dataset.

Figure 5:
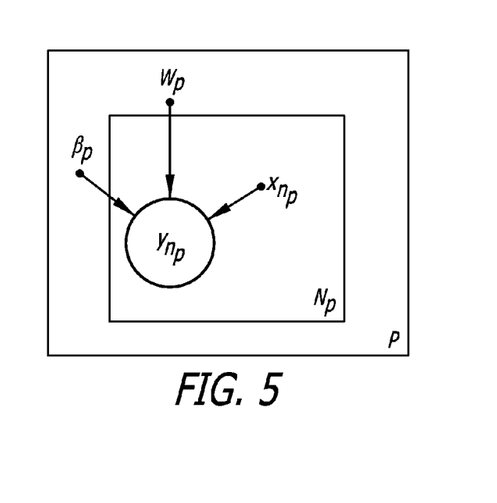
FIG. 5 illustrates a graphical representation of a least-squares regression.

FIG. 5 illustrates a graphical representation of a least-squares regression. The dots represent numbers or parameters, the filled circle is an observed random variable.

—Bayesian Linear Regression (BLR)

Bayesian linear regression (BLR) may adopt a Bayesian approach to the linear regression problem by introducing a prior probability distribution over $w_p$. Once again, the linear model mapping a movement descriptor to energy expenditure may be expressed as:

$$Y_p = w_p^T X_p + \epsilon I, \epsilon \sim \mathcal{N}(0, \beta_p^{-1}) \quad (5)$$

$$y_{n_p} = w_p^T x_{n_p} + \epsilon, \epsilon \sim \mathcal{N}(0, \beta_p^{-1}) \quad (6)$$

$$p(y_{n_p}|x_{n_p}, w_p, \beta_p) = \mathcal{N}(y_{n_p}; w_p^T x_{n_p}, \beta_p^{-1}) \quad (7)$$

where $\epsilon$ is a noise parameter, $x_{n_p} = (1, x_{n_p,1}, \ldots x_{n_p,D})^T$ is the derived function space consisting of fixed nonlinear functions of the input variables of dimension D, and $w_p = (w_{p,0}, \ldots, w_{p,D})^T$ are the weights. A Gaussian prior, $p(w_p) = \mathcal{N}(w_p; 0, \alpha_p^{-1} I)$, may be chosen over the model parameters $w_p$ in Equation. 1, where $\alpha_p$ is a hyper parameter. The optimal prediction for a new data point may be given by the predictive distribution:

$$p(y_{*p}|x_{*p}, Y_p, \alpha_p, \beta_p) = \mathcal{N}(m_p^T x_{*p}, \sigma_p^2(x_{*p})) \quad (8)$$

$$\sigma_p^2(x_{*p}) = \beta_p^{-1} + x_{*p}^T S_p x_{*p} \quad (9)$$

$$S_p^{-1} = \alpha_p I + \beta_p X_p^T X_p \quad (10)$$

$$m_p = \beta_p S_p X_p^T Y_p \quad (11)$$

Learning the model may amount to learning $\{m_{N_p}, S_{N_p}, \alpha_p, \beta_p\}$ for each person p. However, simultaneously learning all these parameters may not be possible because of cyclical dependence. An iterative approach using the following EM algorithm for Bayesian linear regression may be adopted instead:

Inputs:

Movement descriptors in the datamatrix form $X_p$ and corresponding energy prediction values $Y_p$.

Initialization:

Initialize, $w_p = (X_p^T X_p)^{-1} X_p Y_p$; $\alpha_p$ and $\beta_p$ as random values.

Define log-likelihood for each person p as:

$$L_p = \log(p(Y_p|\alpha_p, \beta_p)) = \frac{D}{2}\ln\alpha_p + \frac{N}{2}\ln\beta_p + -\frac{\beta_p}{2}\|Y_p - Xm_p\|^2 - \frac{\alpha_p}{2}\|m_p\|^2$$

Repeat until Log-likelihood converges:

M-Step:

$$\alpha_p = \frac{D}{\|m_p\|^2 + \text{trace}(S_p)}$$

$$\beta_p = \frac{N}{\|Y_p - X_p m_p\|^2 + \text{trace}(X_p^T S_p X_p)}$$

E-Step:

$$S_p = (\alpha_p I + \beta_p X_p^T X_p)^{-1}$$

$$m_p = \beta_p S_p X_p^T Y_p$$

Recalculate Likelihood.

The output prediction of BLR (equations 8 and 9) may involve computing a mean $m_N$ and a variance $\sigma_{N_p}^2(x)$. A variance estimate may allow the user to evaluate how "confident" the algorithm is of its prediction and provide the necessary tool to evaluate the goodness of prediction of an unseen data point. Also, it can be seen from Equation 9 that, if an additional point $x_{N_p+1}$ were added, the resultant variance $\sigma_{N_p+1}^2(x_p) < \sigma_{N_p}^2(x_p)$. This may tend to the limit $$N \to \infty \sigma_N^2(x_p) = \frac{1}{\beta}$$

or the intrinsic noise in the process. Thus, BLR may reflect the higher precision in prediction with the availability of larger quantities of data through a smaller variance. The use of a prior α may help guard against over-fitting. α and β may be derived purely from the dataset without needing a separate validation dataset.

Figure 6:
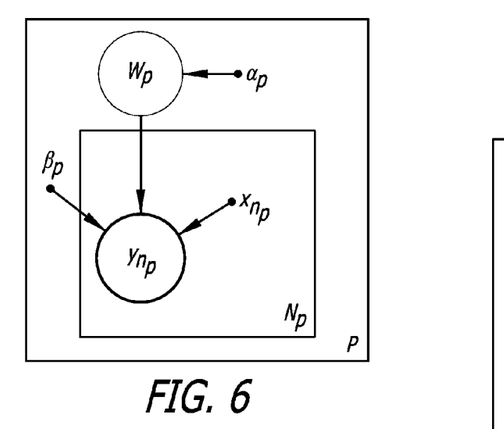
FIG. 6 illustrates a graphical representation of a Bayesian linear regression.

FIG. 6 illustrates a graphical representation of a Bayesian linear regression. The dots represent numbers or parameters, the filled circle is an observed random variables, and the unfilled circle is a hidden random variables.

—Gaussian Process Regression)

Given a set of training points $\{(x_{n_p}, y_{n_p})\}_{n_p=1}^{N_p}$ such that:

$$y_{n_p} = f(x_{n_p}) + \epsilon, \epsilon \sim \mathcal{N}(0, \beta_p^{-1} I) \quad (12)$$

a Gaussian process regression model (GPR) may estimate a posterior probability distribution over functions $\{f(x_{n_p})\}_{n_p=1}^{N_p}$ evaluated at points $\{x_{n_p}\}_{n_p=1}^{N_p}$ such that any finite subset of the functions is a joint multivariate Gaussian distribution. Consequently, for a given set of points $X_p = \{x_{n_p}\}_{n_p=1}^{N_p}$, a corresponding vector may be expressed as $\mathcal{F}_x = \{f(x_{n_p})\}_{n_p=1}^{N_p}$ that belongs to a multivariate Gaussian distribution:

$$\mathcal{F}_{X_p} \sim \mathcal{N}\{\mu_{N_p}(X_p), K_{N_p}(X_p, X'_p)\} \quad (13)$$

where $\mu_{N_p}(X_p) = [\mu(x_{1_p})^T \mu(x_{2_p})^T \ldots \mu(x_{N_p})^T]^T$ and $K_{N_p}(X_p, X'_p)$ is the $N_p \times N_p$ kernel function whose each elements is the covariance value $k(x_{i_p}, x_{j_p})$. A key idea in GPR may be that the similarity between two function outputs, $f(x_{n_p})$ and $f(x_{n_{p'}})$, may depend on the input values, $x_{n_p}$ and $x_{n_{p'}}$ and may be by the kernel $k(x_{n_p}, x_{n_{p'}})$. To completely specify a GP, it may be enough to specify $\mu_{N_p}(X_p)$ and $K_{N_p}(X_p, X'_p)$. By definition, each $f(x_{n_p})$ may be marginally Gaussian, with mean $\mu(x_{n_p})$ and variance $k(x_{n_p}, x_{n_p})$.

Typically, for ease of implementation, the mean of the dataset may be subtracted from each data point so that the mean function is 0. To reflect that similar feature vectors with small interpoint Euclidean distance may be more likely to correspond to the same output energy consumption measure, and to capture the inherent common structure represented by feature vectors due to an underlying periodicity in walking, the radial basis function kernel may be chosen. Further, to capture the fact that there may be only access to noisy observations of the function values, it may be necessary to add the corresponding covariance function for noisy observations. The complete kernel function can be expressed in element by element fashion as:

$$k(x_{n_p}, x'_{n_p}) = \sigma_f^2 \cdot e^{-\frac{1}{2l^2}|x_{n_p} - x'_{n_p}|^2} + \sigma_n^2 \delta_{ij} \quad (14)$$

where $\sigma_f^2$ is the signal variance, l is a length scale that determines strength of correlation between points, and $\sigma_n^2$ is the noise variance.

For a new point $x_{*p}$ there may exist a corresponding target quantity $f(x_{*p})$. Since $f(x_{*p})$ also belongs to the same GP, it can be appended to the original training set to obtain a larger set.

$$\mathcal{F}_{X_p \cup x_{*p}} \sim \mathcal{N}\{\mu_{N_p+1}(X_p \cup x_{*p}), K_{N_p+1}(X_p \cup x_{*p}, X_p \cup x_{*p}^{me})\} \quad (15)$$

$$K_{N_p+1} = \begin{pmatrix} K_{N_p} & k_*(12) \\ k_*^T & k \end{pmatrix} \quad (16)$$

where $k_{*p}$ has elements $k_p(x_{n_p}, x_*)$ for $n_p = 1, \ldots, N_p$ and $k(x_{i_p}, x_{j_p})$ is defined in Equation 14. Using properties of Gaussians and the definition of GPs, it may follow that, for a new test point, $p(y_{*p}|x_{*p}, X_p, Y_p) = \mathcal{N}(f(x_{*p}); m(x_{*p}), \sigma_{x_{*p}}^2)$. Because this joint distribution is Gaussian by definition:

$$m(x_{*p}) = k_{*p}^T K_{N_p}^{-1} Y_p \quad (17)$$

$$\sigma^2(x_{*p}) = k - k_{*p}^T K_{N_p}^{-1} k_{*p} \quad (18)$$

Equations 17 and 18 summarize key advantages of GPR. Again, the use of a probabilistic model to obtain a mean and variance for each prediction may allow the user to assess the confidence of each prediction. In contrast to BLR however, GPR may be non-parametric: its model complexity may increase with larger quantities of data as evident from the increasing size of the kernel matrix. GPR may avoid the process of explicitly constructing a suitable feature function space by dealing instead with kernel functions. As the kernel implicitly contains a non-linear transformation, no assumptions about the functional form of the feature space may be necessary. This may allow dealing with non-linear maps without having to construct non-linear function spaces. The motivation behind considering this algorithm was to determine whether using a nonlinear probabilistic map(GPR) offers benefits over a linear probabilistic map(BLR) in terms of increased prediction accuracy.

Figure 7:
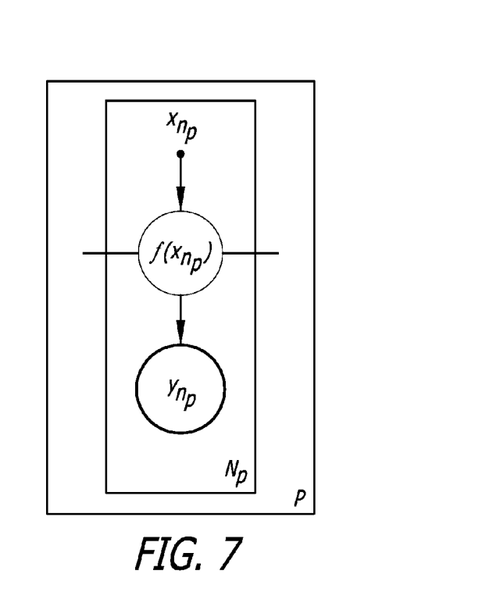
FIG. 7 is a graphical representation of Gaussian process regression.

FIG. 7 is a graphical representation of Gaussian process regression. The dot represents numbers or parameters, the filled circle is an observed random variable, and the unfilled circle is a hidden random variables. The solid horizontal line indicates that all random variables are linked by a single function.

Normalized Energy Expenditure Models Across People

In this part, the more general problem of predicting energy expenditure given the movement and physiological parameters viz. $p(y_{n_p}|x_{n_p}, Phys_p)$ is considered. Two cases are considered: The case of rest and the case of movement.

—Predicting Resting Energy Expenditure Using Physiological Descriptors

In the case of rest, movement may be a constant (viz. 0 movement) and so it may be sufficient to consider $p(y_{n_p}|Phys_p)$. Each person may have only one value of resting energy, so only $p(y_p|Phys_p)$ and $Y_p = y_p$ may be considered. The approach may be similar to the Bayesian linear regression case as outlined above, except that, instead of having movement descriptors $x_{n_p}$ as the inputs, the physiological descriptors may be the input. The linear model mapping a movement descriptor to energy expenditure may be expressed as:

$$y_p = w^T Phys_p + \epsilon, \epsilon \sim \mathcal{N}(0, \beta^{-1}) \quad (19)$$

$$Y = PHYS w + \epsilon I \quad (20)$$

where $\epsilon$ is a noise parameter, $Phys_p = (1, Phys_p^1, \ldots Phys_p^M)^T$ is the derived function space consisting of fixed nonlinear functions of the input variables of dimension D, and $w = (w^0, \ldots, w^M)^T$ are the weights. w may be an M-dimensional model parameter that describes how the physiological descriptors for person p map to resting energy. A Gaussian prior, $p(w) = \mathcal{N}(w; 0, \alpha^{-1} I)$ may be chosen over the model parameters w in Equation 1, where $\alpha$ is a hyperparameter. The optimal prediction for a new data point may be given by the predictive distribution:

$$p(y_{*p}|Phys_{*p}, Y, \alpha, \beta) = \mathcal{N}(m^T x_{*p}, \sigma_p^2(x_{*p})) \quad (21)$$

$$\sigma^2(Phys_{*p}) = \beta^{-1} + Phys_{*p}^T S Phys_{*p} \quad (22)$$

$$S^{-1} = \alpha I + \beta PHYS^T PHYS \quad (23)$$

$$m = \beta S PHYS^T Y \quad (24)$$

Learning the model may amount to learning $\{m, S, \alpha, \beta\}$. Instead, an iterative approach using the following EM algorithm for Bayesian linear regression may be adopted:

Inputs:
Physiological descriptors in the datamatrix form PHYS and corresponding rest energy values Y.

Initialization:
Initialize, $w = (PHYS^T PHYS)^{-1} PHYS^T Y_p$; $\alpha$ and $\beta$ as random values.

Define log-likelihood as:

$$L = \log(p(Y_p|\alpha, \beta)) = \frac{M}{2}\ln\alpha + \frac{N}{2}\ln\beta + -\frac{\beta_p}{2}\|Y_p - PHYS m\|^2 - \frac{\alpha}{2}\|m\|^2$$

Repeat until Log-likelihood converges:
M-Step:

$$\alpha = \frac{D}{\|m\|^2 + \text{trace}(S)}$$

$$\beta = \frac{N}{\|Y - PHYS m\|^2 + \text{trace}(PHYS^T S PHYS)}$$

E-Step:

$$S = (\alpha I + \beta PHYS^T PHYS)^{-1}$$

$$m = \beta S PHYS^T Y$$

Recalculate Likelihood.

—Predicting Energy Expenditure Using Movement and Physiological Descriptors

When both movement and physiological differences exist, the following may need to be estimated: $p(y_{n_p}|x_{n_p}, Phys_p)$. A two-level linear approach may be adopted. Assume that each output energy value, $y_{n_p}$ is linearly dependent on input $x_{n_p}$. This can be expressed as:

$$y_{n_p} = w_p^T x_{n_p} + \epsilon, \epsilon \sim \mathcal{N}(0, \beta_p^{-1}), \quad (25)$$

$$\text{or } y_{n_p} \sim \mathcal{N}(y_{n_p}; w_p^T x_{n_p}, \beta_p^{-1}). \quad (26)$$

$$\text{generally, } Y_p = w_p^T X_p + \epsilon I, \epsilon \sim \mathcal{N}(0, \beta_p^{-1}), \quad (27)$$

$$\text{or } Y_p \sim \mathcal{N}(Y_p; X_p w_p, \beta_p^{-1} I). \quad (28)$$

where, $x_{n_p} = (1, x_{n_p,1}, \ldots, x_{n_p,D})^T$ is the derived function space consisting of fixed nonlinear functions of the input variables of dimension D and $w_p = (w_{p,0}, \ldots, w_{p,D})^T$ are the weights. Here, each person's $w_p$ may be a D-dimensional personal model parameter that describes how the movement descriptors for person p map to energy consumption for that person. $\beta_p$ may be a noise term which incorporates noise in readings. For each participant, physiological descriptors determined by $Phys_p$ and the complete set for all P people, $PHY=\{Phys_p\}_{p=1}^P$ may be given. In the second level of this model, the following may be modeled: top-down dependence of each person's model parameters, $w_p$ on their physiological features $Phys_p$ and a "population" parameter k. Each component $w_{p,m}$ (m=1, 2, ... D) of $w_p$ may follow the relation:

$$w_{p,l} \sim \mathcal{N}(w_{p,l}; k_l^T Phys_p, \alpha_p^{-1} I), l \in (0,1, \ldots D) \quad (29)$$

where $\alpha_p$ is a noise term that incorporates noise in the mapping from $Phys_p$ to $w_{p,m}$. Each $w_p$ in turn may influence energy predictions $y_{n_p}$ for an input $x_{n_p}$.

If there are M physiological parameters, then the dimension of each $k_m$ may also be M. Thus, the overall parameter $k=[k_1\ k_2 \ldots k_D]^T$ may be a D×M matrix.

The HLM may combine P personal regression models in two ways. First, the local regression coefficients $w_p$ may determine energy values for each person. Second, the different coefficients may be connected through the population-level parameter k. The HLM may capture the inherent similarity in walking across different people while accounting for variations in the mapping between individual walking styles and energy consumption.

—Training the Model

Training the hierarchical linear regression model may be equivalent to learning individual $w_p$'s, the overall parameter k as well as the noise parameters $\{\beta_p\}_{p=1}^P$, $\{\alpha_p\}_{p=1}^P$. The following log-likelihood function may need to be maximized:

$$L = \sum_{p=1}^{P} \left( \frac{N_p}{2} \log \beta_p + \frac{M}{2} \log \alpha_p - \left( \frac{\beta_p}{2} \|Y_p - X_p \mu_p\|^2 + \frac{\alpha_p}{2} \|\mu_p\|^2 \right) - \frac{1}{2} \ln |S_p| \right)$$

$$S_p = (\alpha_p I + \beta_p X_p^T X_p)^{-1}$$

$$\mu_p = \sum_{p}^{-1} (\beta_p X_p^T Y_p + \alpha_p m_p)$$

$$m_{p,l} = Phys_p^T k_l$$

Once again, the appearance of cross-terms in the differential of this log-likelihood may not allow direct estimates of the parameters and variables. So, resort may be made to an approximate method using the EM algorithm. FIG. 5 describes the algorithm that may be used to learn this model.

The following is an EM algorithm that learns the parameters of the hierarchical linear model:

Inputs:

Physiological descriptors in the datamatrix form PHYS and corresponding rest energy values Y.

Initialization:

Initialize, $w_p = (X_p^T X_p)^{-1} X_p^T Y_p$; $\alpha_p$ and $\beta_p$ as random values.

Define log-likelihood as:

$$L = \sum_{p=1}^{P} \left( \frac{N_p}{2} \log \beta_p + \frac{M}{2} \log \alpha_p - \left( \frac{\beta}{2} \|Y_p - X_p \mu_p\|^2 + \frac{\alpha_p}{2} \|\mu_p\|^2 \right) - \frac{1}{2} \ln |S_p| \right)$$

Repeat until Log-likelihood converges:
M-Step:

$$k_l = (Phys_p Phys_p^T) \mu_{p,l}$$

$$m_{p,l} = Phys_p^T k_l$$

$$\alpha_p = \frac{D}{\|\mu_p - m_p\|^2 + \text{trace}(S_p)}$$

$$\beta_p = \frac{N_p}{\sum_{n_p=1}^{N_p} \|Y_p - X_p \mu_p\|^2 + \text{trace}(X_p^T S_p X_p)}$$

E-Step:

$$m_{p,l} = Phys_p^T k_m$$

$$S_p = (\alpha_p I + \beta_p X_p^T X_p)^{-1}$$

$$\mu_p = (\alpha_p I + \beta_p X_p^T X_p)^{-1} (\beta_p X_p^T Y_p + \alpha_p m_p)$$

Recalculate Likelihood.

From the algorithm: the confidence of each $w_p$ (measured by $\alpha_p$) may be proportional to how close the mean $\mu_p$ approximates what the predicted mean is from other people and what the inherent noise is in the person's model. Likewise the intra-person prediction may be a weighted combination of what the higher level prediction is from other people (given by $\alpha_p m_p$) and what the individual experimental noise levels are ($\beta_p X_p^T Y_p$). After convergence, these may represent a balanced prediction that is consistent across people.

—Inference

Given the model, energy values may be predicted for a new person P+1 with physiological parameters given by $Phys_{P+i}$, using the equation:

$$w_{P+1,l} \sim \mathcal{N}(w_{P+1}; Phys_{P+1}^T k_l, \alpha_{P+1}^{-1}) \forall l \in \{1,2, \ldots D\}.$$

$$y_{n_{P+1}} \sim \mathcal{N}(y_{n_{P+1}}; w_{P+1}^T x_{n_{P+1}}, \beta_{P+1}^{-1}) \forall n_{p+1} \in \{1,2, \ldots N_{P+1}\}.$$

$\alpha_{P+1}$ and $\beta_{P+1}$ may be set to be the average of $\alpha_p$'s and $\beta_p$'s over all people.

—A Note on Initialization

Since there are a large number of model parameters and the EM algorithm may only converge to a local optimum, good initialization may be key for the algorithm to work. Fortunately, there is a good initialization set for each of these parameters as the estimates given by the Bayesian linear regression algorithm. Using Bayesian linear regression, P individual models may be trained and posterior estimates for $\{w_p \sim \mathcal{N}(\mu_p, \Sigma_p), \alpha_p, \beta_p\}_{p=1}^P$ may be obtained. These models may be used to train a higher level Bayesian linear regression model mapping individual $w_{p,l}$'s to $k_l$'s across people. These initial estimates may be fed into the model and start the training.

—Physiological Descriptors

The physiological descriptors used to describe a person during rest may include height, weight, BMI, gender, resting heart rate, and nonlinear combinations. The descriptors used to describe a person during walking may include height, weight, BMI, gender, resting heart rate, resting energy expenditure, and nonlinear combinations. Height and weight may be indicators of the size of a person. BMI may be an indicator of fat content. Resting heart rate and resting energy expenditure may be indicators of fitness.

—Other Approaches

—Weight Normalized Bayesian Linear Regression

Another approach to generalized modeling of energy expenditure may be to consider weight-scaled energy expenditure values. Each energy expenditure value $y_{n_p}$ may be scaled by a power of that person's weight:

$$y_{n_p,scaled} = \frac{y_{n_p}}{\text{Weight}^s},$$

$s \in \mathbb{R}$. All persons p may be grouped into one "pseudo-person" with the original energy expenditure value replaced by the weight-scaled value. The standard individual BLR model from the section above may be applied.

—Nearest Neighbor Bayesian Linear Regression

Another approach to generalized modeling energy expenditure may be for a given person p, consider top P' with the "most similar" physiological characteristics and train a personalized model for them. These models may be trained individually and their results may be averaged in a weighted fashion. A PCA (principal component analysis) operation on PHYS may be performed. PCA is a standard operation that may reduce the dimensionality of a space by projecting input data into a smaller set of orthogonal dimensions that preserve variance. The values corresponding to the first 3 eigenvectors from the PCA may be stored in a computer data storage system and the reduced space 3-dimensional space $PHYS_{reduced}$ may be kept. For a given person p, the top P' may be obtained by ranking all people by their Euclidean distance from p in the reduced-PCA space. Each of these people may also be assigned a distance-weight $$d_{p,p'} = \frac{1}{\text{Euclidean Distance}(p, p')}.$$

Once the models are trained, each of them may be used to make a prediction for the person p. The final value may be the weight sum of all predictions $$\frac{\sum_{p'} \text{Prediction}(p')d_{p,p'}}{\sum_{p'} d_{p,p'}}.$$

On-Phone Intervention and Coaching Techniques

This section describes the idea of intervening in one's lifestyle by making them stay more active. A goal of this intervention technique may be to reduce the total sedentary time that someone has and the duration of each sedentary time. Being active has widespread applications in weight control, preventing breast and prostrate cancer, and reducing risk of cardiovascular diseases.

Let a given day be divided into arbitrary units of time $U_i$. Typical units may include hour-wise (i∈{1, 2 . . . , 24}), 1 minute (i∈{1, 2 . . . , 1440}), or 5 minute intervals (i∈{1, 2 . . . , 288}). In each of these units of time, a person may have the option to perform a set of activities. These activities may include sleeping, sitting, standing, walking, running, or a specialized activity. Performing each of these activities may have a caloric expenditure associated with it. For example, sleep may have a caloric expenditure rate of 1.5 kcal/min, rest may have a caloric expenditure rate of 2 kcal/min, and walking may have a caloric expenditure between 4 kcal/min and 8 kcal/min. These numbers may depend on the physiological descriptors of the person in question, and can be obtained using the techniques outlined above. Each person, depending on their physiological descriptors, may have certain daily caloric requirements that they may wish to satisfy. A person also consumes food and that may result in a net increase in calories in the body.

The problem of intervention can be stated as how to pick the right set of activities for each of these time intervals so that a certain objective is minimized. One possible objective is to ensure that the net caloric intake of being active and consuming food has to be negative. Another possible objective is to disconnect intake and consumption and to simply ensure that the net calories consumed per day is greater than some minimum recommended value.

A set of algorithms may help achieve this. The solution may be based on historical and current movement sensing on the phone. This may provide access to data that can then be used to adjust goals and suggest actions in real-time. Movement and calories consumed may be recorded in real-time and stored in a computer data storage system using the techniques described in the previous section. Then, based on the user's limitations and current consumption, different actions in the minutes left may be suggested. This can be done on an hourly, daily, or weekly schedule. The most appropriate may be a weekly scale, since this may help offset changes in calorie consumption due to daily variations (e.g. more meetings in a day than usual, falling sick for a few days, etc.). The phone software application may be configured to provide these in the form of a visual, audible, and/or vibratory notification in a just-in-time fashion.

—Rule-Based Intervention

One approach may be to apply a set of rules to decide the right time to intervene. The following steps may be taken:

The user inputs times during which he/she does not want to be disturbed. For example, every person may need between 6 and 8 hours of sleep in a day. Additionally, due to daily schedule limitations, a person might be in a set of meetings that require them to be sedentary. The device will refrain from intervening during those times.

The device continuously senses whether the person is at rest or not. This may be done by calculating the relative movement of the phone using descriptors similar to that described above. If the device senses that the person has not moved for a certain amount of time (the default value of this time may be between 10 and 60 minutes, such as 45 minutes, or the user may be allowed to set this amount), and that their calorie consumption is close to resting levels, and if there is no conflict with the first rule, then the device notifies the user to do something active such as walk (for at least five minutes). The application may continue to record what the user does, again using the smartphone. These calories may then be added to the person's calorie count. This process is not limited to merely testing for movement. It could instead test to see if the person has not walked enough or has not run or has been sitting, whatever parameters the person wants to set. This may be decided by the application context in which the technology is used.

The user can schedule a time when he/she wants to be active, for example, go for a run or a walk. The device may intervene at those particular times and count calories at that time.

—Social-Based Intervention

Another intervention approach, which may be used in addition to or instead of relying on the phone to intervene, may be to share the user's daily computed calorie expenditure data with a group of trusted people. These can include friends, close relatives, or persons with a similar lifestyle. The mobile software app can be configured to provide these trusted people with the user's daily calorie expenditures using a network communication system to which the smartphone has access. Each of these trusted persons can then monitor and track the user's progress. If they find that the user has not been active for a while, they can send a message to the user, such as through text, e-mail, or a phone call, encouraging the user to be more active. Users can also share notes with other people describing their thoughts.

The user can similarly be sent reports on the calorie expenditures of the members of his support group over the network communication system and can provide similar encouragement to each of them when they are deficient in their efforts. Mutual support can be an important component in promoting self-efficacy and self-perception for behavioral change.

Closely related may be the idea of visualizations for community activity monitoring. Here the software application can keep track of the points earned by multiple people in a group and then use the sum of all of these points in the group to build a virtual object. This can be a metaphorical object like a garden or a virtual army, for example. Different people can contribute to this virtual object. If a person is more active, for example, that activity measure may be converted into graphical objects. Rules may be supplied that define how the virtual object will develop based on how active the community is. The virtual object may develop only if each contributor makes a certain number of points and only if all of them make a certain number of points in total, for example. This can provide real-time feedback on how a person is doing wellness wise compared to other people in his group, while preserving the privacy of each member, as their individual scores may not be disclosed to the phone user.

A group of people, or individuals members of that group, can participate in a contest, such as a game, with another group of people or with individual members of the other group. The contest may be configured to provide each group, or each member of each group, with advantages or disadvantages in the contest based on their respective group totals.

—Schedule-Based Intervention

In this intervention technique, people may be provided a daily schedule depending on their goals for the day/week and their achievements so far. This may frame the problem in the form of an integer linear program. Let a given day be divided into arbitrary units of time $U_i$. Typical units may include, for example, hour-wise (i∈{1, 2 . . . , 24}), 1 minute (i∈{1, 2 . . . , 4440}), or 5 minute intervals (i∈{1, 2 . . . , 288}). In each instant of time, a user can pick certain activities $A_{ij}$ (activity j at time i) to perform. For the sake of illustration, there may be four activities: sitting, standing, walking, and running (encoded by numbers 1, 2, 3, 4). Each activity may have certain calorie points $C_j$ corresponding to how many calories can be burned performing that activity.

An objective may be to ensure a certain minimum calorie requirement: $\Sigma_i \Sigma_j A_{ij} C_j \geq M$, where M is the minimum requirement for the day. There may be the following constraint: $\Sigma_j A_{ij}=1$, $A_{ij}=\{0,1\}$. This may encode the idea that a user can perform only one of a given set of activities. If a person schedules sleep or meetings, then those particular times cannot be used for walking or running. For example, someone may set a particular set of times $T_{sleep}$. That constraint may be encoded as $A_{i1}=1$, $A_{ij}=0$, $\forall j=\{1, 2, 3\}$, $\forall i \in T_{sleep}$. Similar constraints can be set for other activities. Additionally, it may not make practical sense to have consecutively alternating minutes of sitting and walking one after the other as these activities may more commonly be performed in bouts of five minutes or more. This can be done by increasing the time steps to 5 minute intervals and ensuring they are selected. Various other constraints can also be encoded. A goal may then be to then solve this linear program for variables $A_{ij}$. This may provide a schedule for when a person can boost their calorie counts for the day and remain active. While this technique provides a fixed schedule for a day, it can also be converted to a "real-time" version by continuously evaluating calories consumed so far (using earlier algorithms), subtracting those calories from the minimum requirement, and then re-learning the variables corresponding to the remainder of the day.

The various algorithms that have been described, as well as the various process steps that have been described, may be performed by a mobile computer system, such as a smartphone, that can readily be carried by a user while that user performs physical activity. The mobile computer system includes one or more processors, tangible memories (e.g., random access memories (RAMs), read-only memories (ROMs), and/or programmable read only memories (PROMS)), tangible storage devices (e.g., hard disk drives, CD/DVD drives, and/or flash memories), system buses, video processing components, network communication components, input/output ports, and/or user interface devices (e.g., keyboards, pointing devices, displays, microphones, sound reproduction systems, and/or touch screens).

The mobile computer system may include software (e.g., one or more operating systems, device drivers, application programs, and/or communication programs). When software is included, the software includes programming instructions and may include associated data and libraries. When included, the programming instructions are configured to implement one or more algorithms that implement one or more of the functions of the computer system, as recited herein. The description of each function that is performed by each computer system also constitutes a description of the algorithm(s) that performs that function.

The software may be stored on or in one or more non-transitory, tangible storage devices, such as one or more hard disk drives, CDs, DVDs, and/or flash memories. The software may be in source code and/or object code format. Associated data may be stored in any type of volatile and/or non-volatile memory. The software may be loaded into a non-transitory memory and executed by one or more processors.

The software that performs the steps and algorithms that have been described may be configured in whole or in part as a mobile application that can be downloaded from a mobile app store and installed in the mobile computer system by the user or by someone else.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and advantages. These also include embodiments in which the components and/or steps are arranged and/or ordered differently.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. Non-transitory, tangible, computer-readable storage media containing a program of instructions configured to cause a mobile computer system that generates a time domain signal that is indicative of steps that a user is taking while carrying the mobile computer system and while running the program of instructions to determine the frequency of those steps by:
   filtering the time domain signal so as to substantially attenuate frequencies that are lower than 0.5 Hz and higher than 10 Hz;
   transforming the filtered time domain signal into a frequency domain signal;
   equating the step frequency with the frequency of the highest peak in the frequency domain signal; and
   communicating the equated step frequency.

2. The media of claim 1 wherein the program of instructions is configured to cause the mobile computer system while running the program of instructions to transform the filtered time domain signal into a frequency domain signal using a fast Fourier transform.

3. The media of claim 1 wherein the program of instructions is configured to cause the mobile computer system while running the program of instructions to determine whether the user is walking or running by:
   filtering a low range of the time domain signal so as to substantially attenuate frequencies that are lower than 0.5 Hz and higher than 2.5 Hz;
   filtering a high range of the time domain signal so as to substantially attenuate frequencies that are lower than 2.5 Hz and higher than 10 Hz;
   transforming the low range filtered time domain signal into a low frequency domain signal using a fast Fourier transform (FFT);
   transforming the high range filtered time domain signal into a high frequency domain signal using a fast Fourier transform (FFT);
   determining that the user is walking if the low frequency domain signal has a peak signal that is larger than any peak signal in the high frequency domain signal;
   determining that the user is running if the high frequency domain signal has a peak signal that is larger than any peak signal in the low frequency domain signal; and
   communicating whether the user has been determined to be walking or running.

4. The media of claim 1 wherein the time domain signal is a composite of:
   a first time domain signal that is representative of movement of the mobile computer system in a first direction;
   a second time domain signal that is representative of movement of the mobile computer system in a second direction that is orthogonal to the first direction; and
   a third time domain signal that is representative of movement of the mobile computer system in a third direction that is orthogonal to the first and the second direction.

5. The media of claim 1 wherein the time domain signal is the signal that has the highest peak level among the following signals, as compared to the highest level peak of the other signals:
   a first time domain signal that is representative of movement of the mobile computer system in a first direction;
   a second time domain signal that is representative of movement of the mobile computer system in a second direction that is orthogonal to the first direction; and
   a third time domain signal that is representative of movement of the mobile computer system in a third direction that is orthogonal to the first and the second direction.

6. The media of claim 1 wherein the program of instructions is configured to cause the mobile computer system while running the program of instructions to communicate that the user is not taking steps if the highest peak in the frequency domain signal is not substantially higher than the other peaks in the frequency domain signal.

7. The media of claim 1 wherein the time domain signal is representative of only vertical movement of the mobile computer system and wherein the program of instructions is configured to cause the mobile computer system while running the program of instructions to determine the time domain signal based on information from the mobile computer system that is indicative of its orientation.

* * * * *